US010912802B2

(12) United States Patent
Navarro López et al.

(10) Patent No.: US 10,912,802 B2
(45) Date of Patent: Feb. 9, 2021

(54) USE OF PROBIOTICS IN THE TREATMENT AND/OR PREVENTION OF PSORIASIS

(71) Applicants: Bionou Research, S.L., Sant Joan d'Alacant (ES); KOROTT, S.L., Alcoy (ES); BIOPOLIS, S.L., Paterna (ES)

(72) Inventors: Vicente Manuel Navarro López, Onil (ES); Ana Adela Ramírez Boscá, Alicante (ES); José Manuel Pérez Orquín, Alcoy (ES); Daniel Ramón Vidal, La Eliana (ES); Salvador Genovés Martínez, Aldaia (ES); María Empar Chenoll Cuadros, La Pobla de Vallbona (ES); Francisco Manuel Codoñer Cortés, Catarroja (ES)

(73) Assignees: Bionou Research, S.L., Sant Joan d'Alacant (ES); KOROTT, S.L., Alcoy (ES); BIOPOLIS, S.L., Paterna (ES)

( * ) Notice: Subject to any disclaimer, the term of this patent is extended or adjusted under 35 U.S.C. 154(b) by 126 days.

(21) Appl. No.: 16/087,584

(22) PCT Filed: Mar. 21, 2017

(86) PCT No.: PCT/EP2017/056719
§ 371 (c)(1),
(2) Date: Sep. 21, 2018

(87) PCT Pub. No.: WO2017/162683
PCT Pub. Date: Sep. 28, 2017

(65) Prior Publication Data
US 2019/0328799 A1 Oct. 31, 2019

(30) Foreign Application Priority Data
Mar. 21, 2016 (EP) ..................................... 16382122

(51) Int. Cl.
| *A61K 35/745* | (2015.01) |
| *A61K 35/747* | (2015.01) |
| *A23L 33/135* | (2016.01) |
| *A61P 17/06* | (2006.01) |
| *A61K 35/741* | (2015.01) |
| *A61K 36/064* | (2006.01) |
| *A61K 35/00* | (2006.01) |

(52) U.S. Cl.
CPC .......... *A61K 35/745* (2013.01); *A23L 33/135* (2016.08); *A61K 35/741* (2013.01); *A61K 35/747* (2013.01); *A61K 36/064* (2013.01); *A61P 17/06* (2018.01); *A23V 2002/00* (2013.01); *A23Y 2220/73* (2013.01); *A23Y 2300/21* (2013.01); *A23Y 2300/49* (2013.01); *A23Y 2300/55* (2013.01); *A61K 2035/115* (2013.01)

(58) Field of Classification Search
None
See application file for complete search history.

(56) References Cited

U.S. PATENT DOCUMENTS

| 8,501,169 B2 * | 8/2013 | Sanz Herranz ...... A61K 35/745 424/93.4 |
| 10,434,127 B2 * | 10/2019 | Robles Rodriguez ........................ C12R 1/225 |
| 10,576,112 B2 * | 3/2020 | Nayak .................. A61K 35/747 |
| 2016/0143963 A1 * | 5/2016 | Martorell Guerola ...................... A23C 11/106 424/93.4 |

FOREIGN PATENT DOCUMENTS

| EP | 2 236 598 A1 | 10/2010 |
| JP | 2004250337 A | 9/2004 |
| KR | 20130049554 A | 5/2013 |
| KR | 20160053447 A | 5/2016 |
| WO | WO 03/070260 A1 | 8/2003 |
| WO | WO 2007/040446 A1 | 4/2007 |
| WO | WO 2012/150269 A1 | 11/2012 |

OTHER PUBLICATIONS

Altschul et al., "Basic Local Alignment Search Tool", Journal of Molecular Biology, vol. 215, pp. 403-410, May 15, 1990.
Arumugam et al., "Enterotypes of the human gut microbiome", Nature, vol. 473, pp. 174-180, May 12, 2011.
Cesaroni et al., "The use of probiotic solution as supplement and restoring agent in some skin pathologies: Pemphigoid lesions, psoriasis, ulcerations and others", Proceedings of the Nutrition Society, vol. 72, E23, Apr. 19, 2013.
Database WPI Week 200461 Thomson Scientific, London, GB; AN 2004-630667 XP002764925, Sep. 9, 2004.
Database WPI Week 201340 Thomson Scientific, London, GB; AN 2013-H88136 XP002764924, May 14, 2013.
Database WPI Week 201645 Thomson Scientific, London, GB; AN 2016-30967X XP002764923, May 13, 2016.
Dave et al., "The human gut microbiome: current knowledge, challenges, and future directions", Translational Research, vol. 160, No. 4, pp. 246-257, Jun. 7, 2012.
Edgar et al., "UCHIME improves sensitivity and speed of chimera detection", Bioinformatics, vol. 27, No. 16, pp. 2194-2200, Jun. 23, 2011.
Extended European Search office search report, dated Jan. 10, 2017, for EP Application No. 16382342.0-1466.
International Search Report, dated Jun. 28, 2017, for PCT Application No. PCT/ES2017/056719.

(Continued)

*Primary Examiner* — Vera Afremova
(74) *Attorney, Agent, or Firm* — Womble Bond Dickinson (US) LLP

(57) ABSTRACT

The present invention is intended for the use of a probiotic composition comprising *Bifidobacterium animalis* subs. *lactis* (*B. lactis*), *Bifidobacterium longum* and *Lactobacillus rhamnosus*, in particular the strains *B. lactis* CECT 8145, *B. longum* ES1 CECT 7347 and/or *L. rhamnosus* CECT 8361, in the treatment and/or prevention of psoriasis outbreaks or psoriasis.

13 Claims, 9 Drawing Sheets

(56) References Cited

OTHER PUBLICATIONS

Jae-Gu Seo et al., "Alleviation of Atopic Dermatitis through Probiotic and Mixed-probiotic Treatments in an Atopic Dermatitis Model", Han-Gug Chugsan Sigpum Hag-Hoeji—Korean Society for Food Science of Animal Resources, vol. 31, No. 3, Jun. 30, 2011, pp. 420-427.

Marcel Martin, "Cutadapt removes adapter sequences from high-throughput sequencing reads", EMBnet.journal, vol. 17, No. 1, pp. 10-12, May 2011, available at: <https://journal.embnet.org/index.php/embnetjournal/article/view/200/479>.

Written Opinion of the International Searching Authority, dated Jun. 28, 2017, for PCT Application No. PCT/ES2017/056719.

Zhang et al., "PEAR: a fast and accurate Illumina Paired-End reAd merger", Bioinformatics, vol. 30, No. 5, pp. 614-620, Oct. 18, 2013.

Ha T ice Kubra Akay et al., "The relationship between bifidobacteria and allergic asthma and/or allergic dermatitis: A prospective study of 0-3 years-old children in Turkey", Anaerobe, vol. 28, Aug. 1, 2014, pp. 98-103.

Klindworth et al., "Evaluation of general 16S ribosomal RNA gene PCRprimers for classical and next-generation sequencing-based diversity studies", Nucleic Acids Research, 2013, vol. 41, No. 1 e1, Aug. 28, 2012.

\* cited by examiner

USE OF PROBIOTICS IN THE TREATMENT AND/OR PREVENTION OF PSORIASIS

CROSS-REFERENCE TO RELATED APPLICATIONS

The present patent application is a national phase application of International Application No. PCT/EP2017/056719, filed Mar. 21, 2017, which claims priority to European Patent Application No. 16382122.6, filed Mar. 21, 2016, the disclosures of which are incorporated herein by reference.

The present invention relates to the use of a probiotic composition for the treatment and/or prevention of psoriasis outbreaks and/or psoriasis. Therefore, the present invention could be encompassed within the field of medicine, particularly in the treatment of skin diseases.

STATE OF THE ART

Psoriasis is an inflammatory and proliferative systemic disease characterized by the appearance of typical skin lesions in the form of multiple erythematous patches with well-defined edges, covered with scaly lesions, mainly localized, but not exclusively, in extensor areas of the limbs and scalp. There is therefore a hyperproliferative component affecting the epidermis, associated with an inflammatory component affecting the dermis. The diagnosis of psoriasis is clinical, not requiring histological confirmation in most cases. The disease presents no characteristic laboratory data. The pathogenesis of psoriasis is not well known and most authors believe that it is a genetically determined skin disorder that would be triggered by various external factors, in the end causing a lymphocytic infiltrate and ultimately, the typical skin lesions of the disease.

It is generally considered that in developed countries psoriasis affects between one percent (1%) and three percent (3%) of the population, although there is variability among European countries. In any case, the psychological, social and economic impact on the population is considerable and comparable to other better-known chronic disorders, such as chronic bronchial disease, diabetes mellitus or depressive disorders.

Due to the alleged immune origin of psoriasis, treatment has been based for years on the use of immunosuppressants, either topical or systemic, to try to stop the immune component of the disease and thus alleviate the symptoms. This disease characteristically shows an elevation of inflammatory markers such as the tumour necrosis factor (TNF) and interleukins IL-12 and IL-23. In recent years notable progress has been made in the treatment thereof through the development of immunomodulatory drugs such as the anti-TNF and monoclonal anti IL-23. These medicaments are, in general, more effective than topical or classic systemic treatments such as cyclosporine or corticosteroids, but in turn cause a high economic cost and can cause side effects in these patients, among others, the onset of latent infectious diseases such as tuberculosis and hepatitis B virus hepatitis, which has conditioned the indication and use of these drugs to certain cases of severe psoriasis. Moreover, with the passage of time in many cases an antibody phenomenon against these drugs occurs, whereby they cease to be effective in controlling psoriasis.

Therefore, the prior art shows the need to develop new useful compounds in the treatment of psoriasis, being effective without causing the individual the typical side effects of classical drugs in the treatment of psoriasis.

DETAILED DESCRIPTION OF THE INVENTION

The authors of the present invention have observed that individuals with psoriasis outbreaks surprisingly exhibit an intestinal microbiota diversity which is very different from that of healthy individuals. Based on this observation, the inventors found that administering a probiotic composition that modifies the intestinal microbiota to an individual suffering from psoriasis, surprisingly allows remission and/or improvement of the evolution of outbreaks of psoriasis in the individual. As shown in the examples accompanying the present description, when the probiotic composition (comprising microorganisms of *Bifidobacterium* sp. and *Lactobacillus* sp.) was administered together with the usual treatment of patients with outbreaks of psoriasis, an additional thirty percent (30%) of cases with complete improvement was observed over that achieved in patients with psoriasis patients (or psoriatic patients) receiving regular chronic treatment but without the aforementioned probiotic composition.

In addition to this beneficial effect on disease progression in patients with an outbreak of active psoriasis, it was also observed that in the months after discontinuation of treatment with the above mentioned probiotic composition, individuals who had received treatment with such composition had fewer outbreaks and, therefore, larger time free of disease than those patients who had not received treatment.

Thus the utility of the probiotic composition described herein for the treatment and/or prevention of psoriasis outbreaks or psoriasis is demonstrated.

Based on this discovery, a number of inventive aspects that will be described in detail below have been developed. Use of the First Probiotic Composition of the Invention in the Treatment of Psoriasis Outbreaks and/or Psoriasis.

In one aspect, the invention relates to a probiotic composition for use in the treatment and/or prevention of outbreaks of psoriasis and/or psoriasis, wherein the probiotic composition comprises the microorganisms *Bifidobacterium animalis* subs. *lactis* (hereinafter *B. lactis*), *Bifidobacterium longum* and *Lactobacillus rhamnosus*.

In the present invention the term "probiotic composition" is that composition comprising at least one microorganism which, when ingested, interacts with the individual's metabolism and produces a beneficial effect in it. In the present invention, the probiotic composition comprises the microorganisms *B. lactis*, *B. longum* and *L. rhamnosus*, hereinafter, "first probiotic composition of the invention".

*B. lactis* is a bacterium commonly used as probiotics, found mostly in yogurt and other dairy products, including infant formula. The scientific classification of *B. longum* is: Kingdom: Bacteria Division: Firmicutes Class: Actinobacteria, Order: Bifidobacteria, Family: Bifidobacteriaceae, Genus: *Bifidobacterium*, Species: *Bifidobacterium animalis* subsp. *lactis*.

*L. rhamnosus* is a bacterium commonly used as probiotics, found mostly in yogurt and other dairy products, including infant formula. The scientific classification of *L. rhamnosus* is: Kingdom: Bacteria Division: Firmicutes Class: Bacilli Order: Lactobacillales, Family: Lactobacillaceae, Genus: *Lactobacillus*, Species: *Lactobacillus rhamnosus*.

Moreover, *B. longum* is a Gram negative, catalase-negative bacterium, rounded in shape, located in the gastrointestinal tract, where it produces lactic acid. The scientific classification of *B. longum* is: Kingdom: Bacteria Division: Firmicutes Class: Actinobacteria, Order: Bifidobacteria, Family: Bifidobacteriaceae, Genus: *Bifidobacterium*, Species: *Bifidobacterium longum*.

In a particular embodiment, the first probiotic composition of the invention comprises *B. lactis* CECT 8145 (and/or strains derived therefrom), *B. longum* ES1 CECT 7347 (and/or strains derived therefrom) and/or *L. rhamnosus* CECT 8361 (and/or strains derived therefrom).

*B. lactis* strain CECT 8145 was isolated from faeces of a healthy and breastfeeding child less than three (3) months old. This strain was deposited on 14 May 2012 under the Budapest Treaty in the Spanish Type Culture Collection as an International Depositary Authority (based in Building 3 CUE, Parc Cientific Universitat de Valencia, C/Catedrático Agustin Escardino, 9, 46980 Paterna (Valencia) SPAIN). The deposit number assigned was CECT 8145.

*L. rhamnosus* strain CECT 8361 was isolated from faeces of a healthy and breastfeeding child less than three (3) months old. This strain was deposited on 27 May 2013 under the Budapest Treaty in the Spanish Type Culture Collection as an International Depositary Authority (based in Building 3 CUE, Parc Cientific Universitat de Valencia, C/Catedrático Agustin Escardino, 9, 46980 Paterna (Valencia) SPAIN). The deposit number assigned was CECT 8361.

*B. longum* strain CECT 7347 was isolated from faeces of a healthy breastfeeding child less than three (3) months old and deposited on 20 Dec. 2007 under the Budapest Treaty in the Spanish Type Culture Collection as the International Depository Authority (based in Building 3 CUE, Parc Cientific Universitat de Valencia, C/Catedrático Agustin Escardino, 9, 46980 Paterna (Valencia) SPAIN). The deposit number assigned was CECT 7347.

The present invention also contemplates those microorganisms or bacteria derived from the microorganisms *B. lactis*, *B. longum* and *L. rhamnosus* (or their corresponding strains *B. lactis* CECT 8145, *L. rhamnosus* CECT 8361 and *B. longum* CECT 7347) and that may be part of the first probiotic composition of the invention as they retain the ability to reduce and/or improve the evolution of psoriasis outbreaks or psoriasis in the individual. Examples of strains or microorganisms derived from strains comprised within the first probiotic composition of the invention may be mutants and genetically modified organisms which show variations in their genome compared to the genome of the strains of the invention, but which do not affect the ability of strains to reduce and/or improve the evolution of psoriasis outbreaks in the individual. Strains derived from *B. lactis*, *B. longum* and *L. rhamnosus* or from strains of *B. lactis* CECT 8145, *L. rhamnosus* CECT 8361 and *B. longum* CECT 7347 can be naturally or intentionally produced by mutagenesis methods known in the art such as for example, but not limited to, the growth of the parent strain in the presence of mutagenic agents or stressors or by genetic engineering directed to the modification, deletion and/or insertion of specific genes. Thus, as indicated above, the present invention also contemplates genetically modified organisms derived from *B. lactis*, *B. longum* and *L. rhamnosus* or from strains of *B. lactis* CECT 8145, *L. rhamnosus* CECT 8361 and *B. longum* CECT 7347, that retain the ability to reduce and/or improve the evolution of psoriasis outbreaks in an individual and, therefore, to be used in the treatment of psoriasis. An example of a test to verify if an organism has the ability to reduce and/or improve the evolution of psoriasis outbreaks in an individual is described in the accompanying examples herein.

Furthermore, the present invention, also contemplates cellular components, metabolites and molecules secreted by *B. lactis*, *B. longum* and *L. rhamnosus* or their corresponding strains *B. lactis* CECT 8145, *L. rhamnosus* CECT 8361 and/or *B. longum* CECT 7347 as well as compositions comprising said components and uses thereof for the treatment and/or prevention of psoriasis outbreaks and/or psoriasis. The cellular components of bacteria could include components of the cell wall (such as, but not limited to, peptidoglycan), nucleic acids, membrane components and other, such as proteins, lipids and carbohydrates and combinations thereof (such as lipoproteins, glycolipids or glycoproteins). Metabolites include any molecule produced or modified by the bacterium as a result of its metabolic activity during growth, its use in technological processes or during storage of the product (first probiotic composition of the invention). Examples of these metabolites include, but are not limited to, organic and inorganic acids, proteins, peptides, amino acids, enzymes, lipids, carbohydrates, lipoproteins, glycolipids, glycoproteins, vitamins, salts, minerals or nucleic acids. Secreted molecules include any molecule secreted or released to the outside by the bacterium during growth, its use in technological processes (for example, food processing or drugs) or during storage of the product. Examples of these molecules include, but are not limited to, organic and inorganic acids, proteins, peptides, amino acids, enzymes, lipids, carbohydrates, lipoproteins, glycolipids, glycoproteins, vitamins, salts, minerals or nucleic acids.

As understood by those skilled in the art, the first probiotic composition of the invention may be formulated for pharmaceutical administration, i.e., forming part of pharmaceutical products to be administered to the subject (either orally, topically, etc.), and/or for food administration, i.e. forming part of the foods consumed in the subject's diet. Therefore, in a particular embodiment, the first probiotic composition of the invention is a pharmaceutical composition and/or a nutritional composition.

The pharmaceutical composition for use in the treatment and/or prevention of psoriasis outbreaks and/or psoriasis is a set of components which is formed at least by microorganisms *B. lactis*, *L. rhamnosus* and *B. longum*, in particular by strains of *B. lactis* CECT 8145, *L. rhamnosus* CECT 8361 and/or *B. longum* CECT 7347 (or strains derived therefrom) at any concentration and which additionally may comprise one or more components or compounds having any biological, pharmacological and/or veterinary useful activity in the prevention and/or treatment of psoriasis outbreaks and/or psoriasis; and/or may comprise one or more components which, upon administration to a subject, may further increase, enhance and/or promote the activity of the strains included in the first probiotic composition of the invention. As understood by one skilled in the art, the additional components or compounds must be compatible with the strains of the first probiotic composition of the invention. In the context of the present invention, the term "pharmaceutical composition" also encompasses veterinary compositions.

Examples of useful components or compounds in the treatment of psoriasis outbreaks and/or psoriasis which can be part of the pharmaceutical composition include, but are not limited to, immune response regulating compounds, such as methotrexate or cyclosporine, retinoid components or compounds such as vitamin D or A, anti-TNF biological drugs, recombinant interleukins or adjuvants useful in the treatment of psoriasis with phototherapy.

In a particular embodiment, the pharmaceutical composition further comprises a pharmaceutically acceptable carrier and/or excipient.

The term "excipient" refers to a substance that helps the absorption of any components or compounds of the first probiotic composition of the invention, namely, of strains of the invention, or stabilizes the components or compounds and/or assists the preparation of the pharmaceutical composition in the sense of giving it consistency or flavours to make it more pleasant. Thus, the excipients may have the function, by way of example but not limited thereto, of binding the components (for example, starches, sugars or cellulose), sweetening, colouring, protecting the active ingredient (for example, to insulate it from air and/or moisture), filling a pill, capsule or any other presentation or a disintegrating function to facilitate dissolution of the components, without excluding other excipients not listed in this paragraph. Therefore, the term "excipient" is defined as that material that included in the galenic forms, is added to the active ingredients or their associations to enable their preparation and stability, modify their organoleptic properties or determine the physico-chemical properties of the pharmaceutical composition and its bioavailability. The "pharmaceutically acceptable" excipient must allow the activity of components or compounds of the pharmaceutical composition, that is, be compatible with the strains of the invention.

The "galenic form" or "pharmaceutic form" is the configuration to which the active ingredients and excipients are adapted to provide a pharmaceutical composition or a drug. It is defined by the combination of the form in which the pharmaceutical composition is presented by the manufacturer and the form in which it is administered.

The "vehicle" or "carrier" is preferably an inert substance. Carrier functions are to facilitate the incorporation of other components or compounds, allow better dosage and administration and/or give consistency and form to the pharmaceutical composition. Therefore, the carrier is a substance used in the drug to dilute any of the components or compounds of the pharmaceutical composition of the present invention to a given volume or weight; or that even without diluting these components or compounds, it is able to allow better dosage and administration and/or give consistency and form to the drug. When the presentation is liquid, the pharmaceutically acceptable carrier is the diluent. The carrier can be natural or unnatural. Examples of pharmaceutically acceptable carriers include, without being limited thereto, water, salt solutions, alcohol, vegetable oils, polyethylene glycols, gelatine, lactose, starch, amylose, magnesium stearate, talc, surfactants, silicic acid, viscous paraffin, perfume oil, monoglycerides and diglycerides of fatty acids, fatty acid esters petroetrals, hydroxymethylcellulose, polyvinylpyrrolidone and the like.

Furthermore, the excipient and the carrier must be pharmacologically acceptable, i.e., the excipient and the carrier are permitted and evaluated so as not to cause damage to the subject to whom it is administered.

In each case the presentation of the pharmaceutical composition will be adapted to the type of administration used. Thus, the composition may be presented in the form of solutions or any other form of clinically permissible administration and in a therapeutically effective amount. The pharmaceutical composition can be formulated into solid, semisolid or liquid preparations, such as tablets, capsules, powders, granules, solutions, suppositories, gels or microspheres. In a particular embodiment, the pharmaceutical composition is formulated for administration in liquid form or in solid form.

In another particular embodiment, the solid formulation is selected from the group consisting of tablets, lozenges, sweets, chewable tablets, chewing gums, capsules, sachets, powders, granules, coated particles or coated tablets, tablet, pills, troches, gastro-resistant tablets and capsules and dispersible strips and films.

In another particular embodiment, the liquid formulation is selected from the group consisting of oral solutions, suspensions, emulsions and syrups.

Likewise, various systems are known that can be used for sustained-release administration of the first probiotic composition of the invention, including, for example, the encapsulation in liposomes, microbubbles, microparticles or microcapsules and the like. The suitable sustained-release forms as well as materials and methods for their preparation are well known in the state of the art. Thus, the orally administrable form of the first probiotic composition of the invention is in a sustained-release form further comprising at least one coating or matrix. The sustained release coating or matrix includes, without limitation, natural semisynthetic or synthetic polymers, water-insoluble or modified, waxes, fats, fatty alcohols, fatty acids, natural, semisynthetic or synthetic plasticizers or a combination of two or more of the same. Enteric coatings can be applied using conventional processes known to those skilled in the art.

In addition to what has been described above, the present invention also encompasses the possibility that the first probiotic composition of the invention may be administered to a subject together with other components or compounds, although these are not part of the first probiotic composition of the invention. Examples of such components or compounds have been mentioned in preceding paragraphs.

In the event that the first probiotic composition of the invention is formulated as a nutritional composition, said nutritional composition may be a food or be incorporated into a food or food product intended for both human and animal consumption. Thus, in a particular embodiment, the nutritional composition is selected from between a food (which may be a food for specific nutritional purposes or medicinal food) and a nutritional supplement.

In the present invention, the term "nutritional composition" refers to that food, which regardless of providing nutrients to the subject who consumes it, beneficially affects one or more functions of the body, so as to provide better health and wellness. In the present invention, said nutritional composition is intended to ease, reduce, treat and/or prevent psoriasis outbreaks and/or psoriasis.

The term "supplement", synonymous with any of the terms "dietary supplement", "nutritional supplement", "food supplement", or "alimentary supplement" or "alimentary complement" refers to products or preparations whose purpose is to supplement the normal diet consisting of sources of concentrated nutrients or other substances with a nutritional or physiological effect. In the present invention, the "substance" which has a nutritional or physiological effect on the individual when the alimentary complement is ingested are the microorganisms *B. lactis*, *L. rhamnosus* and *B. longum*, in particular the strains *B. lactis* CECT 8145, *L. rhamnosus* CECT 8361 and/or *B. longum* CECT 7347, which are part of the first probiotic composition of the invention. The food supplement may be in single or combined form and be marketed in dosage form, i.e. in capsules, pills, tablets and other similar forms, sachets of powder, ampoules of liquids and drop dispensing bottles and other similar forms of liquids and powders designed to be taken in a single amount.

There is a wide range of nutrients and other elements that may be present in alimentary complements including, among others, vitamins, minerals, amino acids, essential fatty acids, fibre, enzymes, plants and plant extracts. Since their role is to complement the supply of nutrients in a diet, they should not be used as a substitute for a balanced diet and intake should not exceed the daily dose expressly recommended by the doctor or nutritionist. The first probiotic composition can also be part of the so-called "food for special groups", i.e. foods that meet specific nutritional needs.

Examples of foods that may comprise the first probiotic composition of the invention (microorganisms B. lactis, L. rhamnosus and B. longum, in particular strains B. lactis CECT 8145, L. rhamnosus CECT 8361 and/or B. longum CECT 7347 (or strains derived therefrom)) include, but not limited to, feed, dairy products, vegetable products, meat products, snacks, chocolates, drinks, baby food, cereals, fried foods, industrial bakery products and biscuits. Examples of milk products include, but are not limited to, products derived from fermented milk (for example, but not limited to, yogurt or cheese) or non-fermented milk (for example, but not limited to, ice cream, butter, margarine or whey). The vegetable product is, for example, but not limited to, a cereal in any form of presentation, fermented (for example, soy yogurt, oat yogurt, etc.) or unfermented, and a snack. The beverage may be, but is not limited to, non-fermented milk. In a particular embodiment, the food product or food is selected from the group consisting of fruit or vegetable juices, ice cream, infant formula, milk, yogurt, cheese, fermented milk, powdered milk, cereals, baked goods, milk-based products, meat products and beverages.

Additionally, the first probiotic composition of the invention may comprise other microorganisms in addition to B. lactis, L. rhamnosus and B. longum, in particular strains B. lactis CECT 8145, L. rhamnosus CECT 8361 and/or B. longum CECT 7347. Thus, in a particular embodiment, the first probiotic composition of the invention further comprises a microorganism selected from the group consisting of Lactobacillus sp., Streptococcus sp., Bifidobacterium sp., Saccharomyces sp., Kluyveromyces sp. and combinations thereof.

In another even more particular embodiment, Lactobacillus sp. is L. rhamnosus, L. delbrueckii subsp. bulgaricus, L. kefir, L. parakefir, L. brevis, L. casei, L. plantarum, L. fermentum, L. paracasei, L. acidophilus, L. paraplantarum or L. reuteri; Streptococcus sp. is St. thermophilus; Bifidobacterium sp. is B. longum, B. breve, B. bifidum, B. catenulatum, B. adolescentis or B. pseudocatenulatum; Saccharomyces is S. cerevisiae or S. boulardii; or Kluyveromyces sp. is K. lactis or K. marxianus.

In another particular embodiment, the composition of the invention is administered to a subject through the diet.

As understood by one skilled in the art, the microorganisms B. lactis, L. rhamnosus and B. longum, in particular the strains B. lactis CECT 8145, L. rhamnosus CECT 8361 and/or B. longum CECT 7347, have to be present in the probiotic composition of the invention in a therapeutically effective amount so that they can exert their effect of easing, reducing, treating and/or preventing psoriasis outbreaks or psoriasis.

In the present invention "therapeutically effective amount" is that amount of the component or compound of the pharmaceutical composition, which when administered to a subject, is sufficient to produce the desired effect. Said component or compound of the pharmaceutical composition refers to the microorganisms B. lactis, L. rhamnosus and B. longum, in particular the strains B. lactis CECT 8145, L. rhamnosus CECT 8361 and/or B. longum CECT 7347. The therapeutically effective amount will vary depending on, for example, age, body weight, general health, sex and diet of the subject, as well as according to the mode and time of administration, excretion rate or drug combination, among other factors.

Thus, in a particular embodiment, the total concentration of microorganisms of B. lactis, L. rhamnosus and B. longum, in particular the strains B. lactis CECT 8145, L. rhamnosus CECT 8361 and/or B. longum CECT 7347 in the composition is between $10^3$ and $10^{12}$ cfu, preferably $10^9$ cfu. In another particular embodiment, the dose of administration of microorganisms B. lactis, L. rhamnosus and B. longum, in particular B. lactis CECT 8145, L. rhamnosus CECT 8361 and/or B. longum CECT 7347, in the composition is between $10^6$ and $10^{12}$ cfu/day, preferably $10^9$ cfu/day, and in another even more particular embodiment, the administration regime is at least once daily, in particular twice daily, and more in particular, three times a day, one with each food intake (breakfast, lunch and dinner).

In another particular embodiment of the first probiotic composition of the invention, the concentration of B. longum, particularly of the strain B. longum CECT 7347, is at least thirty percent (30%) with respect to the total concentration of microorganisms present in the composition, preferably at least 31%, 32%, 33%, 34% or 35% relative to the total concentration of microorganisms present in the first probiotic composition of the invention.

In another even more particular embodiment, the concentration of B. longum is at least 35% with respect to the total amount of microorganisms present in the first probiotic composition of the invention, the concentration of B. lactis is at least 35% with respect to the total amount of microorganisms present in the first probiotic composition of the invention, and the concentration of L. rhamnosus is at least 30% with respect to the total amount of microorganisms present in the first probiotic composition.

Due to the capacity of the first probiotic composition of the invention to reduce and/or improve the evolution of outbreaks of psoriasis in the individual as well as to improve the evolution of psoriasis once the intake of the probiotic composition has been suspended, this invention contemplates the use of the probiotic composition of the invention in the prevention and/or treatment of psoriasis outbreaks and/or psoriasis.

In the present invention the term "subject" is equivalent to the term "individual"; so both terms can be used interchangeably herein. "Subject" means, in addition to any individual, any animal belonging to any species. Examples of subjects include, but are not limited to, animals of commercial interest such as birds (hens, ostriches, chicks, geese, partridges, etc.), rabbits, hares, pets (dogs, cats, etc.), sheep, goat cattle (goats, etc.), swine (boars, pigs, etc.), equine livestock (horses, ponies, etc.), cattle (bulls, cows, oxen, etc.); animals of hunting interest, such as stags, deer, reindeer, etc.; and humans. However, in a particular embodiment, the subject is a mammal, preferably the mammal is a human being of any race, sex or age.

In the present invention the term "prevention" means to avoid occurrence of the disease or pathological condition in an individual, particularly when the individual has predisposition for the pathological condition, but has not yet been diagnosed. In the present invention, the disease or pathological condition is an outbreak of psoriasis or psoriasis.

In the present invention, the term "treat" or "treatment" comprises inhibiting the disease or pathological condition, i.e., stopping its development; relieving the disease or pathological condition, i.e., causing regression of the disease or pathological condition; and/or stabilizing the disease or pathological condition in an individual. In the present invention, the disease or pathological condition is a psoriasis outbreak or psoriasis.

In the present invention the term "psoriasis" is a chronic inflammatory dermatosis that causes outbreaks and whose elemental lesion is erythema as a manifestation of the underlying inflammatory process and an epidermal hyperproliferation due to a failure in epidermal cell replication which results in the appearance on skin of hyperkeratosis or cluster of scales at skin layer level.

Psoriasis can manifest in many forms and places other than the skin. Thus, in a particular embodiment, the psoriasis is selected from the group consisting of plaque psoriasis, palmar-plantar psoriasis, scalp psoriasis, inverse psoriasis affecting skin folds, guttate psoriasis or eruptive psoriasis, nail psoriasis and arthropatic psoriasis. The subject may simultaneously suffer from one or more of these manifestations of psoriasis.

In the present invention the term "psoriasis outbreaks" refers to the reappearance of typical erythematous scaly lesions of psoriasis after a period of absence of clinical signs of psoriasis.

Second Prebiotic Composition of the Invention

In another aspect, the present invention relates to a probiotic composition comprising the microorganisms *Bifidobacterium animalis* subs. *lactis* (hereinafter *B. lactis*), *Bifidobacterium longum* and *Lactobacillus rhamnosus*, wherein the concentration of *B. longum* with respect to the total concentration of microorganisms present in the composition is at least 30%.

The term "probiotic composition" has been previously defined and is applicable to this inventive aspect. Hereinafter, "second probiotic composition of the invention" is the probiotic composition comprising the microorganisms *B. lactis*, *B. longum* and *L. rhamnosus*, wherein the concentration of *B. longum* with respect to the total concentration of microorganisms present in the second composition of the invention is at least 30%, preferably at least 35%. In a particular embodiment, each microorganism is in a proportion of at least 30% relative to the total concentration of microorganisms present in the second probiotic composition of the invention.

In a particular embodiment, the concentration of *B. longum* with respect to the total concentration of microorganisms present in the composition is at least 31%, 32%, 33%, 34% or 35%.

In another even more particular embodiment of the second probiotic composition, the concentration of *B. longum* is at least 35% relative to the total of microorganisms present in the second probiotic composition of the invention, the concentration of *B. lactis* is of at least 35% relative to the total of microorganisms present in the second probiotic composition of the invention, and the concentration of *L. rhamnosus* is at least 30% relative to the total of microorganisms present in the second probiotic composition of the invention.

As explained in the preceding inventive aspect, *B. lactis* and *L. rhamnosus* are bacteria commonly used as probiotics, which are mainly found in yogurts and other dairy products, including infant formula. Moreover, *B. longum* is a Gram negative, catalase-negative bacterium, rounded in shape, located in the gastrointestinal tract, where it produces lactic acid. In a particular embodiment, the second probiotic composition of the invention comprises strains of *B. lactis* CECT 8145, *B. longum* ES1 CECT 7347 and/or *Lactobacillus rhamnosus* CECT 8361. More references on these strains can be found in the preceding inventive aspect.

Also, all the particular embodiments described for the first probiotic composition of the invention are applicable to the second probiotic composition of the invention, for example, but not limited to, the following:

The probiotic composition is a pharmaceutical composition or a nutritional composition, wherein the pharmaceutical composition comprises a pharmaceutically acceptable carrier and/or excipient, it is formulated for administration in liquid or solid form and wherein the nutritional composition is a food or nutritional supplement.

The probiotic composition comprises additional microorganisms such as *Lactobacillus* sp., *Streptococcus* sp., *Bifidobacterium* sp., *Saccharomyces* sp., *Kluyveromyces* sp. or combinations thereof.

The total concentration of microorganisms of the strains *B. lactis*, *L. rhamnosus* and *B. longum* in the composition is between $10^3$ and $10^{12}$ cfu, preferably $10^9$ cfu.

The dose of administration of the microorganisms *B. lactis*, *L. rhamnosus* and *B. longum*, in particular *B. lactis* CECT 8145, *L. rhamnosus* CECT 8361 and/or *B. longum* CECT 7347, in the composition is between $10^6$ and $10^{12}$ cfu/day, preferably $10^9$ cfu/day.

The administration regime is at least once a day, in particular, twice a day, and more particularly, three times a day, one with each food intake (breakfast, lunch and dinner).

In another aspect, the present invention relates to the second probiotic composition of the invention for use as a medicament.

In another aspect, the present invention relates to the second probiotic composition of the invention for use in the treatment and/or prevention of psoriasis outbreaks and/or psoriasis.

Method of Treatment and/or Prevention of Inflammatory Skin Diseases

In another aspect, the invention relates to a method for the treatment of psoriasis outbreaks or psoriasis in a subject, hereinafter, method of treatment of the invention comprising administering a probiotic composition to an individual who presents an inflammatory skin disease, wherein the probiotic composition comprises the strains *B. lactis*, in particular, *B. lactis* CECT 8145, *L. rhamnosus*, in particular, *L. rhamnosus* CECT 8361 and *B. longum*, in particular, *B. longum* CECT 7347.

All particular terms, definitions and embodiments of previous inventive aspects are applicable to the treatment method of the invention.

Throughout the description and claims the word "comprise" and its variants are not intended to exclude other technical characteristics, additives, components or steps. For those skilled in the art, other objects, advantages and characteristics of the invention will become apparent in part from the description and partly from the practice of the invention. The following examples and figures are provided by way of illustration and are not intended to limit the scope of the present invention.

EXAMPLES

Figure 1:
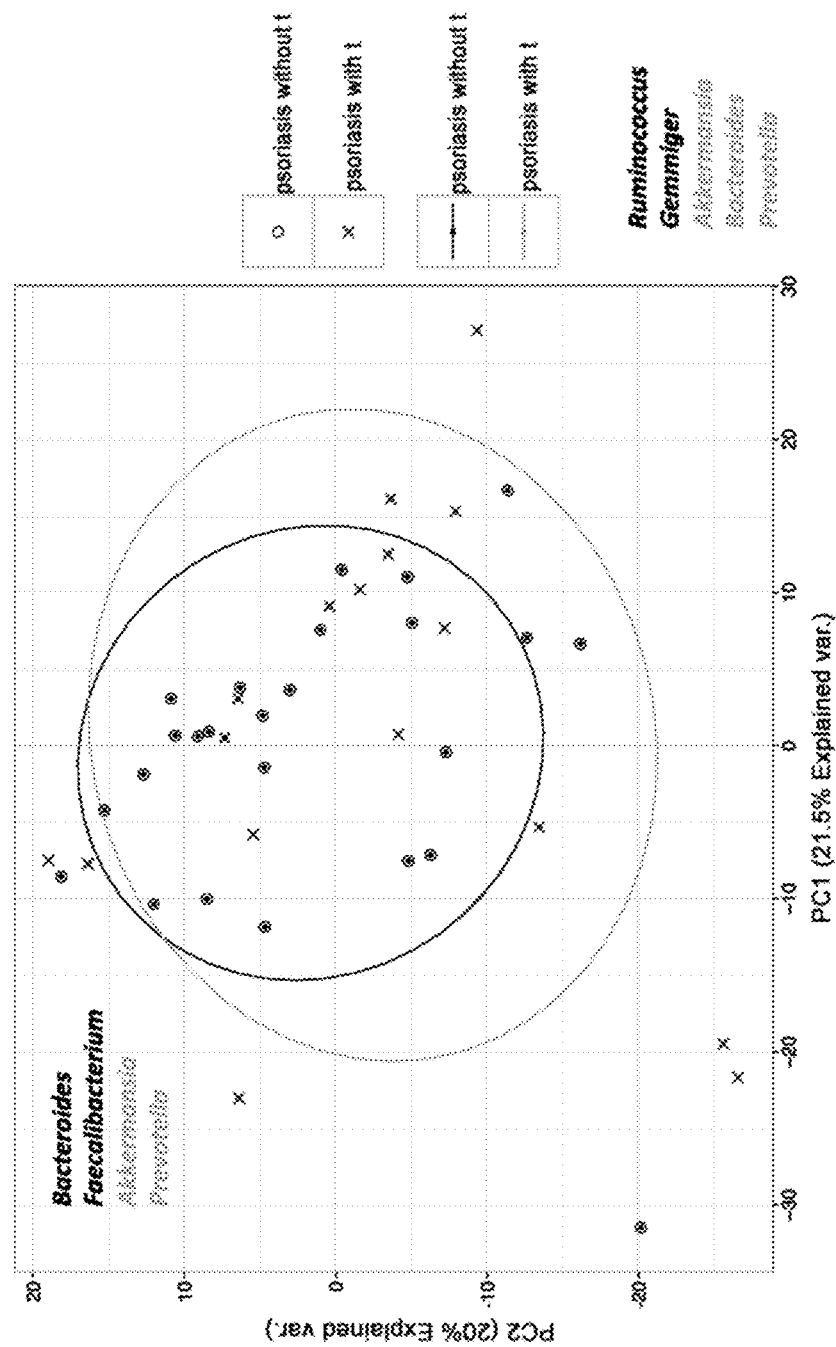
FIG. 1 is a diagram showing the analysis of the main components of the microbiological profiles of samples of psoriatic patients, with translocation ("x" and grey) and without translocation ("o" and black).

The invention is illustrated below by tests performed by the inventors, which show the properties of the probiotic composition of the invention.

Example 1—Determination of Bacterial Microbiota in Patients with Psoriasis 1.1 Material and Methods Based on the samples of faeces of psoriatic patients with and without translocation, extraction of genetic material (DNA) was performed using a combination of mechanical and enzymatic disruption of cell walls and membranes to increase the yield of extraction and not bias the presence of bacteria with cell wall (Gram +), whose presence may be diminished due to a lack of rupture of the wall by ordinary methods of extraction. This genetic material obtained in the extraction was measured in quality and quantity using a Nanodrop 2000 ThermoScientific to inspect ratios 260 nm/280 nm and 260 nm/230 nm that mark the extraction quality (presence of PCR inhibitors, pigment, etc.). Later, after verifying the quality of the genetic material of the samples, libraries of massive sequencing were conducted capturing the hypervariable region v3-v4 of the bacterial 16s rRNA gene (based on Klindworth A, et al. (2013) Nucleic Acids Res 41: e1) according to the protocol described by Illumina for analysis of the microbial composition based on the capture of 16s rRNA. Each library was quantified with Quant-iT PicoGreen by Invitrogen and mixed together in equimolar way for subsequent sequencing.

Samples were sequenced in MiSeq platform in a combination of 300 "Paired-End" cycles. The resulting FASTQ files were treated to ensure high quality sequence analysis. For this purpose, a quality control was conducted consisting of:

1. Joining the ends to reconstruct unique sequences using the program 'pear' v0.9.6. (Zhang J, et al (2014) Bioinformatics 30 (5):614-20).
2. Elimination of sequencing adapters and capture primers from the hypervariable regions V3 and V4 with the program cutadapt version 1.9.1. (Martin M (2011) EMBnet.journal [S.L.], 17 (1): 10-12. ISSN 2226-6089.).
3. Elimination of low quality sequences using FASTX-ToolKit version 0.91.
4. Elimination of chimeras resulting from PCR using the UCHIME program (December 2015) (Edgar R C, et al (2011) Aug. 15; 27 (16): 2194-200) and the last database of chimeras.

The resulting samples were compared against a database of 16S rRNA (NCBI) using a BLAST type local alignment (Altschul S F, et al (1990) J. Mol Biol. 215: 403-410).

Each of the sequences in which a score of 95% identity was obtained was inspected at different taxonomic of levels phylum, Family, Genus and Species.

The R statistical package was used for the construction of statistics and graphs for principal component analysis (PCA).

1.2 Results

From faeces of patients affected by psoriasis, a study of the microbial composition of the intestine was performed in order to determine:

1. If the intestinal microbial composition of psoriasis patients having bacterial DNA translocation of intestinal origin in peripheral blood samples is the same or if there are differences with regard to psoriasis patients without bacterial DNA translocation of intestinal origin.
2. If the composition of the intestinal microbiome of psoriasis patients is different from the composition in healthy population.

This study was based on the capture of the hypervariable region v3-v4 of the bacterial 16s rRNA gene, as indicated above, and subsequent sequencing in a MiSeq Illumina platform (Metagenomic Sequencing Library Preparation Protocol. (ILLUMINA).

Microbiological profiles of samples of patients with and without translocation seem to have no significant differences globally, as can be seen in FIG. 1, wherein patients with translocation ("x" and grey) and without translocation ("o" and black) are distributed evenly.

FIG. 1 shows that the samples that are distributed more to the right of the graph have a greater presence of the genera *Ruminococcus* and Gemmiger and decreased Akkermansia, *Bacteroides* and *Prevotella*, while those at the top of the graph have increased *Bacteroides* and *Faecalibacterium* and decreased Akkermansia and *Prevotella*; accordingly, the existence of an own microbiome in patients with psoriasis could be asserted.

Figure 2:
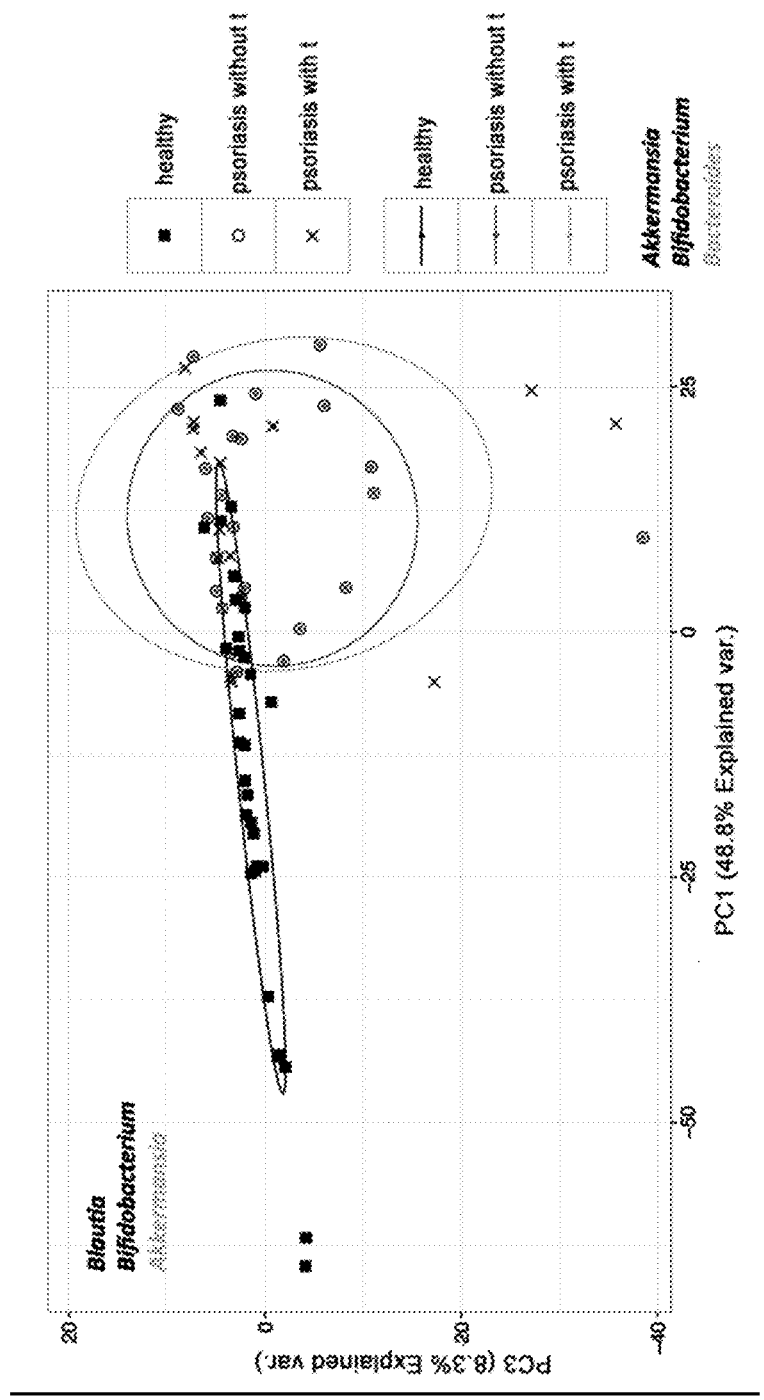
FIG. 2 is a diagram showing the analysis of the main components of the microbiological profiles of samples of psoriatic patients, with translocation ("x" and grey) and without translocation ("o" and dark grey) versus healthy subjects.

When these patients with psoriasis were compared against data of microbial composition in healthy population, it was found that there was a difference between healthy subjects and psoriatic patients, as seen in FIG. 2. In principle, differences are observed between data of healthy population and patients with psoriasis, although there are data for healthy population that are shared or are close to those of some patients with psoriasis, but in general there are differences in the composition of bacteria present in the digestive tract.

Figure 3:
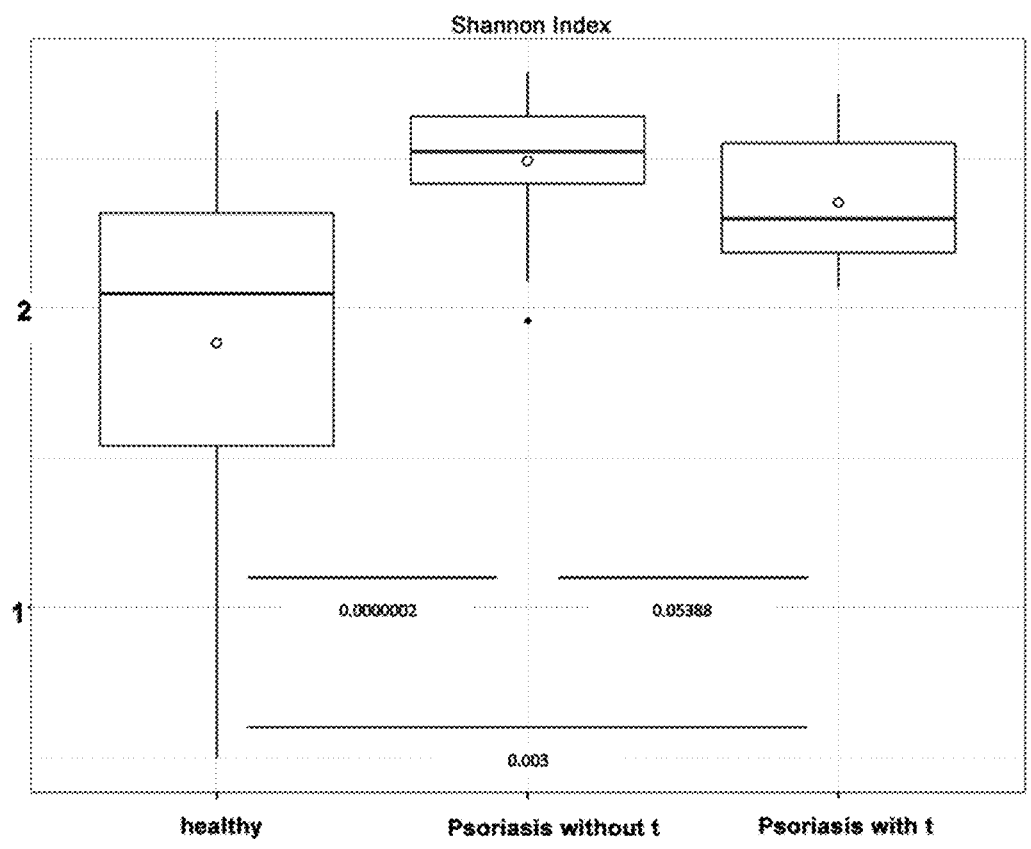
FIG. 3 is a diagram showing the variability analysis of samples of psoriatic patients with translocation and without translocation, compared with that of the healthy population. The statistics significances after applying a Wilcoxon test are shown in the figure.

This can be seen in more detail when the variability of bacterial populations between healthy population and psoriatic patients is analysed based on the variability detected with Shannon's index (FIG. 3). If we compare overall healthy population with patients with psoriasis with translocation, the latter have greater variability (p-value=0.003). Similarly, patients with psoriasis without translocation also have higher variability compared to the healthy population (p-value=0.0000002), in this case the diversity among patients with translocation being somewhat greater. When we compare the diversity among patients with translocation and those without translocation, this is not significant although it is near the limit of significance (p-value=0.054).

Although there is great variation in microbial populations of the digestive tract of each individual, epidemiological studies suggest that the microbiota of almost all of them can be classified as belonging to three distinct categories known as enterotypes (Arumugam et al., (2011) Nature 473:174-180). This classification is based on the predominance in each of these three enterotypes of members of the genera *Bacteroides*, *Prevotella* or *Ruminococcus*. Enterotype 1 is referred to when *Bacteroides* is predominant, enterotype 2 if *Prevotella* is predominant and enterotype 3 when *Ruminococcus* is predominant (Dave et al., (2012). Trans. Res. 160, 246-257).

Figure 4:
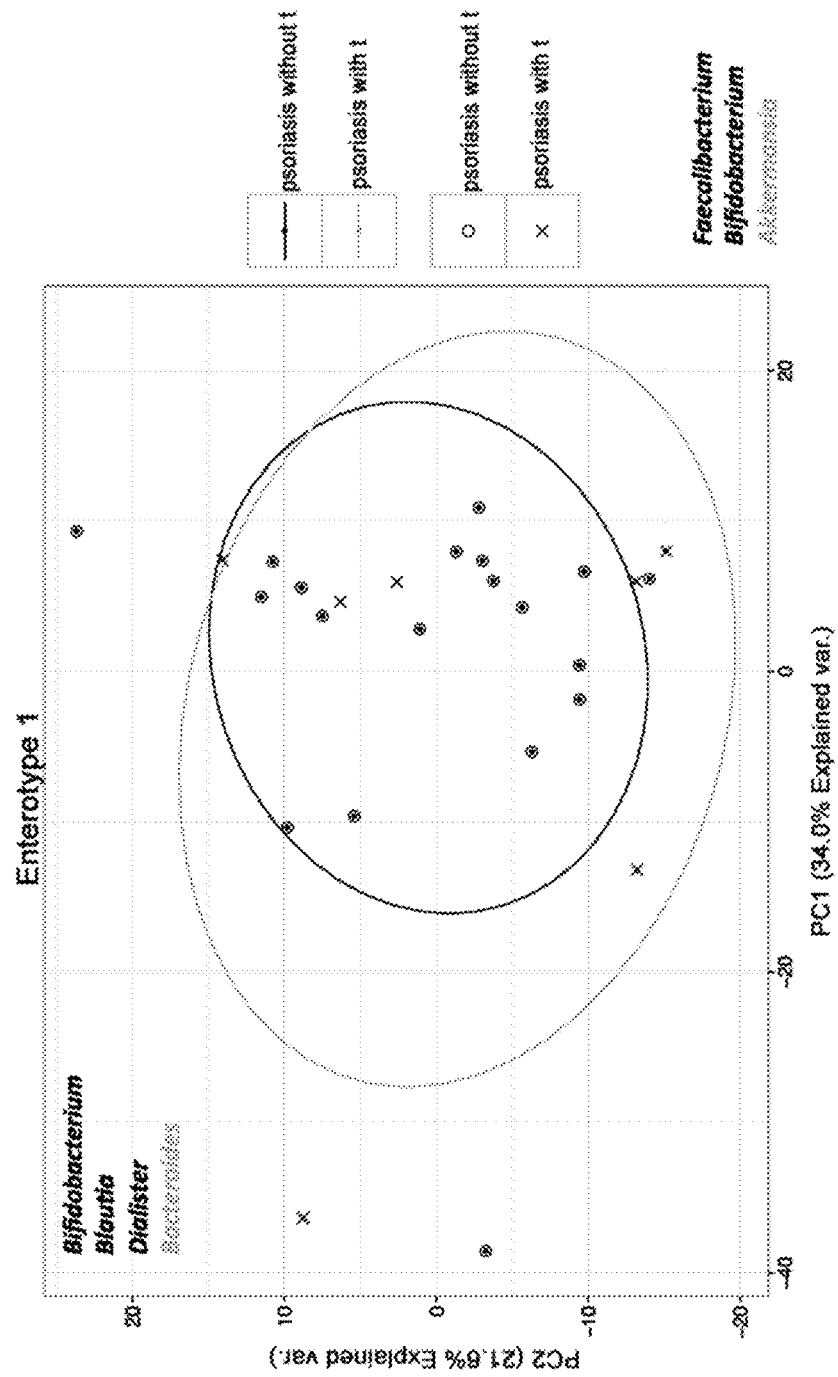
FIG. 4 is a diagram showing the analysis of main components of psoriatic patients with and without translocation, belonging to or classified as enterotype 1. The most represented genera in the samples located on the right and top of the figure are shown in black and those which are least represented in this same situation are shown in grey. Samples in the lower left corner show the opposite behaviour: genera that are marked in black are less abundant and genera that are marked in grey are more abundant.

Following this way of stratifying the data, patients with psoriasis were classified according to the predominance of *Bacteroides* (ent1), *Prevotella* (INT2) or *Ruminococcus* (Ent3) to see if there were differences between patients with translocation of bacterial DNA in blood and those without translocation. FIG. 4 shows the differences in terms of patients classified as belonging to enterotype 1. As noted, there are no clear differences between patients with translocation and those without.

Figure 5:
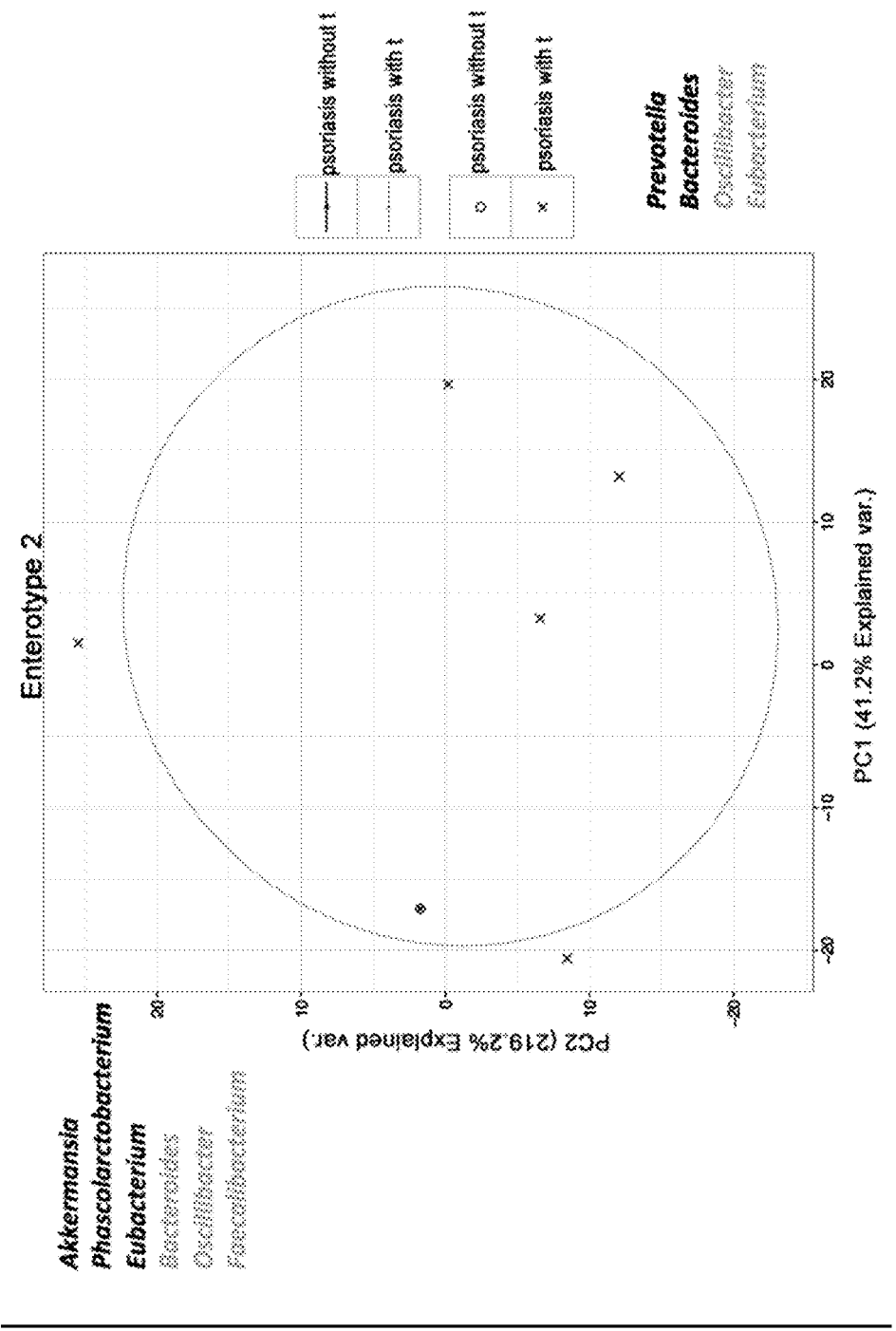
FIG. 5 is a diagram showing the analysis of the main components of psoriatic patients with and without translocation, belonging to or classified as enterotype 2. The most represented genera in the samples located on the top right of the figure are shown in black and those which are least represented in this same situation are shown in grey. Samples in the lower left corner show the opposite behaviour: genera that are marked in black are less abundant and genera that are marked in grey are more abundant.

FIG. 5 shows the same as FIG. 4 but in terms of classification of patients in enterotype 2. In this case, there is a clear trend of patients with psoriasis with translocation, because of the six individuals with psoriasis classified as enterotype 2, all except one suffer from translocation of bacterial DNA.

Figure 6:
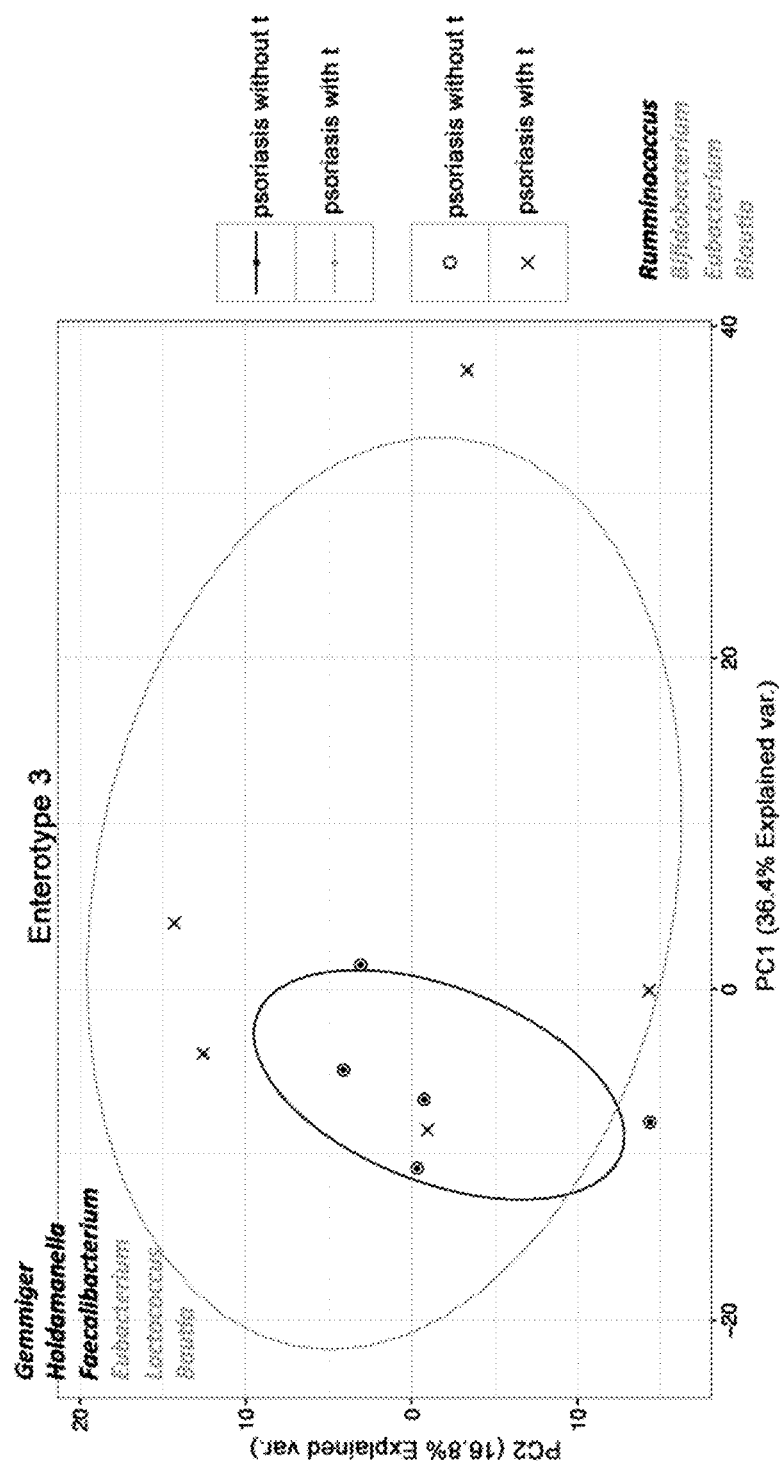
FIG. 6 is a diagram showing the analysis of the main components of psoriatic patients with and without translocation, belonging to or classified as enterotype 3. The most represented genera in the samples located on the top right of the figure are shown in black and those which are least represented in this same situation are shown in grey. Samples in the lower left corner show the opposite behaviour: genera that are marked in black are less abundant and genera that are marked in grey are more abundant.

As is the case of enterotype 1, in the case of patients classified as enterotype 3 (FIG. 6), there are no differences in prevalence between patients with translocation of bacterial DNA in blood and those without, although it is noted that patients with translocation exhibit more variability than those without.

1.3 Conclusion

Patients with psoriasis have a similar intestinal microbial composition, with or without translocation of bacterial DNA in blood.

This intestinal microbial composition is, in turn, different from the intestinal microbial composition found in healthy population.

By classifying psoriatic patients in the same enterotypes/groups as the healthy population, it can be seen that patients classified in enterotype 2 (increased amount of *Prevotella* genus) are mostly patients with translocation.

Overall, variability in the microbial composition of faeces of psoriatic patients with translocation is greater than that from psoriatic patients in which the presence of bacterial DNA in blood is not detected (patients without translocation).

Example 2—Study of the Effect of the Intake of the Probiotic Composition in Patients with Psoriasis 2.1 Material and Methods
Objective of the Clinical Study
Main Objective:
To study the evolution in a group of patients with psoriasis by administering the probiotic composition under study together with the chronic standard treatment of these patients, assessing the percentage of improvement in these patients compared to what was obtained according to the literature described and own experience. To this end a group of patients who did not take the probiotic composition of the invention was used to estimate differences in the percentage of cured patients at the end of an observation period.

Secondary Objectives:
To assess the levels of biomarkers of systemic inflammation in blood TNF-α, IF-γ and Interleukin 1B.
To assess the severity of psoriasis using the PASI test in both groups of patients with and without the presence of bacterial translocation of intestinal origin.

Probiotic Composition
The study used the probiotic composition (Formulated 004023) comprising the strains *Bifidobacterium lactis* CECT 8145, *Bifidobacterium longum* ES1 CECT 7347 and *Lactobacillus rhamnosus* CECT 8361. The concentration of such strains relative to the amount of microorganisms present in the composition is 35% for *B. longum* ES1%, 35% for *B. lactis* and 30% for *L. rhamnosus*.

Clinical Trial Methodology
Type of study: dietary supplement intervention
Study Design: Observational of intervention
Ultimate objective, classification: safety/efficacy
Intervention model: two arms
Primary objective: Treatment

| Arms in the study | Allocated intervention |
|---|---|
| Active comparator: probiotic composition of the invention. The daily dose was administered by a single daily tablet dose containing about 300 mg of the probiotic composition. | Two arms: with the probiotic composition vs placebo |

The primary objective of the study was to test whether the percentage of patients with clinical response to treatment (reduction of at least 75% in value of the PASI at week 12 compared to baseline, at the beginning of the study) was higher in the group treated with the probiotic composition in the group of patients without intake of the probiotic composition.

The PASI and PGA measurement was performed in each of the visits scheduled in the study to quantify the variation that may exist in the average value of these indices between visits (intragroup comparison).

As a secondary objective, the analytical comparison of the response to treatment was carried out. This was conducted by quantifying the values of inflammatory markers: TNF-α, IF-γ, IL-1b, IL-16, IL-12 and by comparing the average of these values at the time of inclusion in the study with the same measurement on the last visit (intragroup comparison).

As a measure to ensure the safety of the probiotic composition under study, all the side effects that appeared during the study were recorded, both those due to the probiotic composition itself and those not due to it, and the results between the two study groups were compared.

Eligibility to Participate in the Trial

To be eligible for evaluation and inclusion in the study, subjects had to meet all the inclusion criteria listed below as well as not to meet any exclusion criteria which are also listed below:

Inclusion Criteria:
  Men and women aged between 18 and 70 years.
  Plaque psoriasis diagnosed at least one year before the study.
  Mild to moderate psoriasis with PASI greater than 6 without a new outbreak of psoriasis (no change in the severity of psoriasis) in the last four weeks.
  Patients able to give informed consent to participate in the study.
  In case of women of childbearing age, prior negative pregnancy test and use of barrier measures during sexual intercourse during their participation in the study.

Exclusion Criteria:
  Crohn's disease, liver cirrhosis, morbid obesity, and infection with human immunodeficiency virus (HIV) or other active infection.
  Use of oral steroids or any other systemic, oral or parenteral treatment used as a treatment for psoriasis in the three months prior to inclusion in the study.
  Use of antibiotics, probiotics and/or prebiotics in the two weeks prior to the beginning of the studio.
  Use of natural products with proven efficacy for health in the two weeks prior to the study (except multiminerals and multivitamins).
  Liver disease with Child Pugh index C, chronic renal failure with creatinine clearance below 50 ml/min and moderate or severe endocrine, neurological or cardiovascular respiratory chronic disease depending on the consideration of researchers in the study and concomitant skin disease prior to the start of the study.
  Pregnancy and lactation.
  Not being able to give informed consent to participate in the study or meet the conditions for any reason.

Variables to be Evaluated in the Test
Primary Study Variables:
  Percentage of patients who showed a change greater than 75% in the PASI in the study group in control visits during the study and/or the end-of-study visit.
  Percentage of patients who showed improvement according to the PGA index (defined as an improvement in the PGA score motivating a change in the category of this severity index at end of study).

Secondary Study Variables:
  Percentage of patients in remission (whitening psoriasis) in control visits during the study and/or at end-of-study visit.
  Differences in values of the PASI and PGA indices from the inclusion visit until the end-of-study visit (intragroup differences).
  Percentage of patients who showed a change greater than 50% (PASI50) in the study group at the end-of-study visit.
  Percentage of patients who remained in analytical remission at the end of the study (normal values of inflammatory markers).
  Differences in mean inflammatory markers studied: TNF-α, IF-γ, IL12, IL1b, IL6 and IL23 by comparing this value at the baseline visit and at end-of-study visit (intragroup differences).
  Percentage of patients with mild, moderate or severe side effects attributed to the study medicament and not attributed to this medicament.

Study Treatment and Number of Patients Studied

Study treatment was performed with the probiotic composition (Formulated 004023) (*Bifidobacterium lactis* CECT 8145, *Bifidobacterium longum* ES1 CECT 7347 and *Lactobacillus rhamnosus* CECT 8361) in the form of 300 mg capsules. Together with the usual psoriasis treatment, a daily capsule was administered orally before the midday meal, every day of the study, as indicated in the data sheet of the probiotic composition. The reference treatment was that routinely administered to patients with psoriasis.

Being a pilot study, the study was conducted with 47 cases of psoriasis, with the interpretation that an improvement in reaching PASI 75 values by more than 20% in the group of patients who received the probiotic composition, over the rate observed in the patients receiving conventional treatment to 12 weeks follow up, would already be considered a clinically significant difference. The results were compared with the data available to the researchers according to routine clinical practice in the treatment of psoriasis outbreaks with the same characteristics.

2.2 Results 47 individuals who met all inclusion criteria and none of the exclusion criteria were recruited. All of them were included in this pilot study. Demographic data and the degree of severity of psoriasis of patients in the two treatment groups were similar at the time of inclusion in the study. Patients were treated for a total of twelve (12) weeks, with monthly visits in which treatment adherence information and results in PASI values of each patient were collected.

Figure 7:
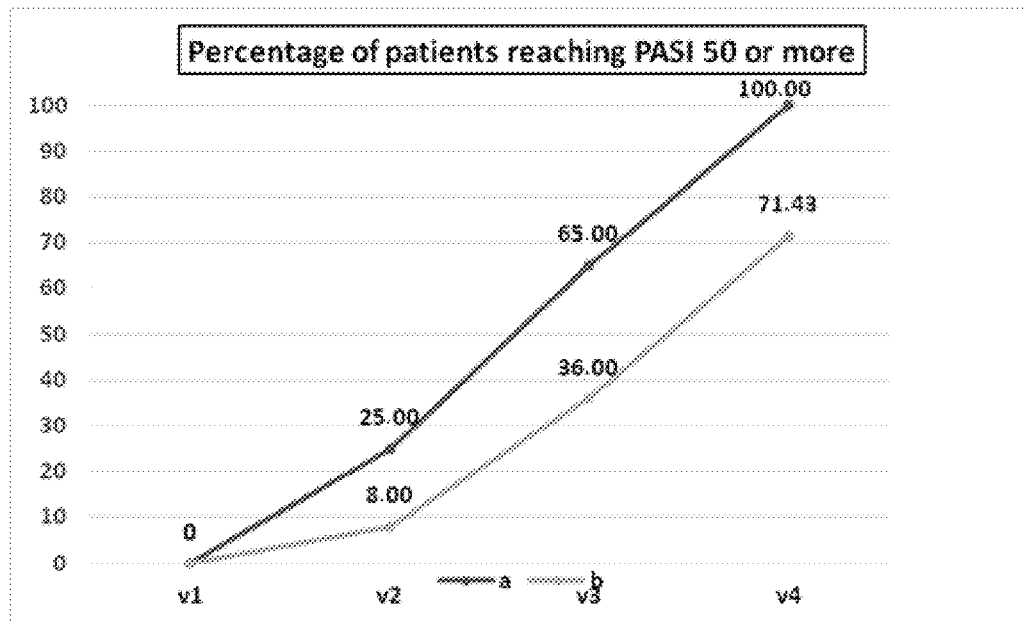
FIG. 7 is a graph showing the percentage of patients with partial response to treatment in the two groups: group a treated with the probiotic composition; group b treated with placebo.
Figure 8:
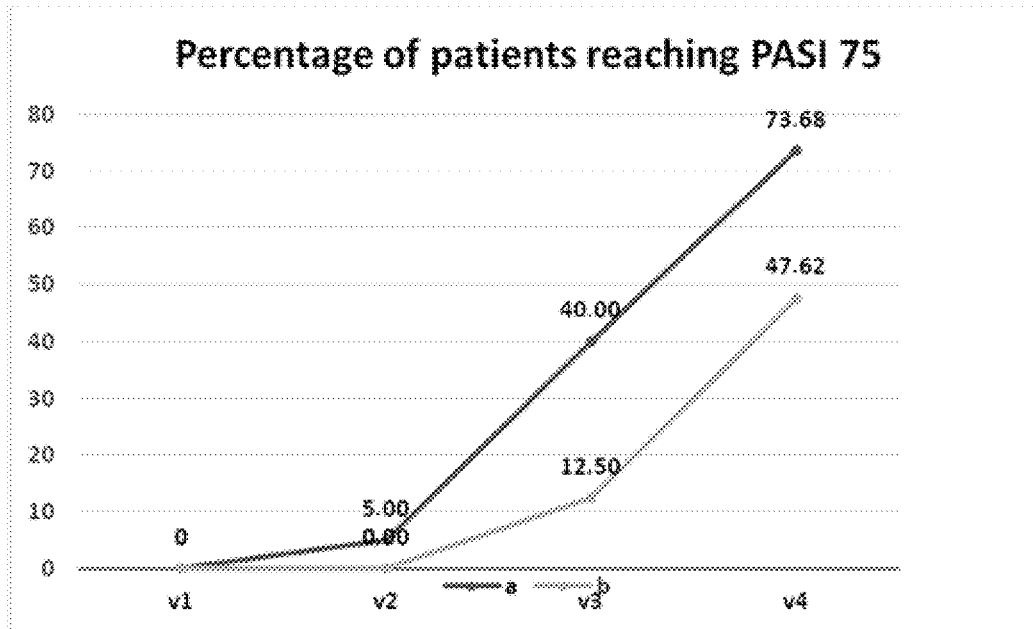
FIG. 8 is a graph showing the percentage of patients with response to treatment in the two groups; group a, treated with the probiotic composition; group b treated with placebo.
Figure 9:
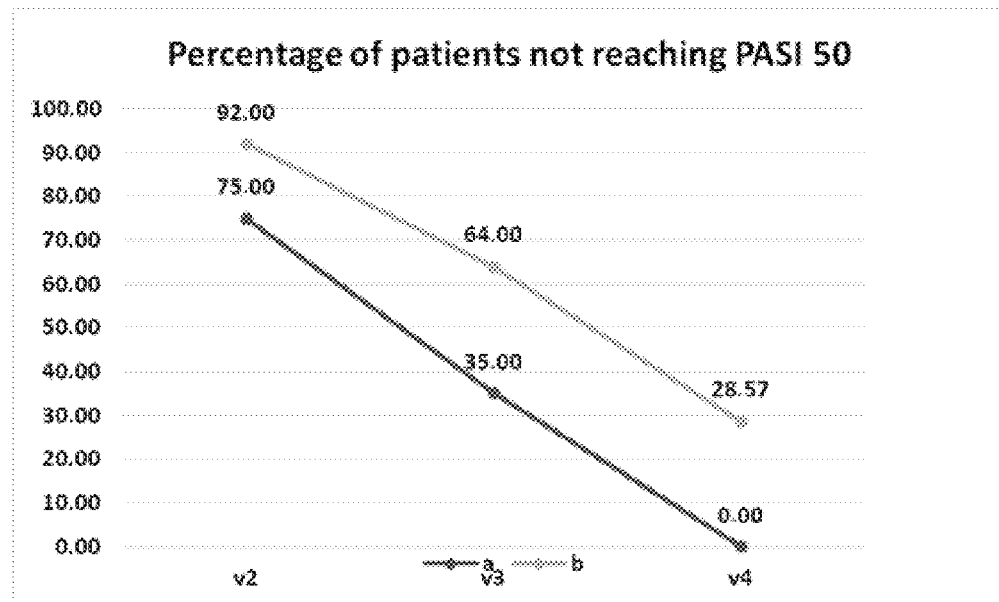
FIG. 9 is a graph showing the percentage of patients with treatment failure in the two groups; group a, treated with the probiotic composition; group b treated with placebo.

After a treatment period of twelve (12) weeks, it was observed that from week 8 there were significant differences with a greater percentage of patients with partial response (PASI over 50%) in the group treated with the probiotic composition both at week 8 and week 12 of follow up (FIG. 7). With regard to the complete response to treatment assessed as PASI improvement greater than 75% compared to baseline, significant differences between the two treatment groups were also found in favour of the group treated with the probiotic composition; these differences were particularly significant from week 8 and continued at week 12, final week of treatment (FIG. 8). Finally, the group treated with the probiotic composition showed no cases without response to treatment understood as PASI improvement of less than 50% at week 12 compared to baseline PASI, while in the group treated with placebo, 28.6% showed no response to treatment.

Figure 10:
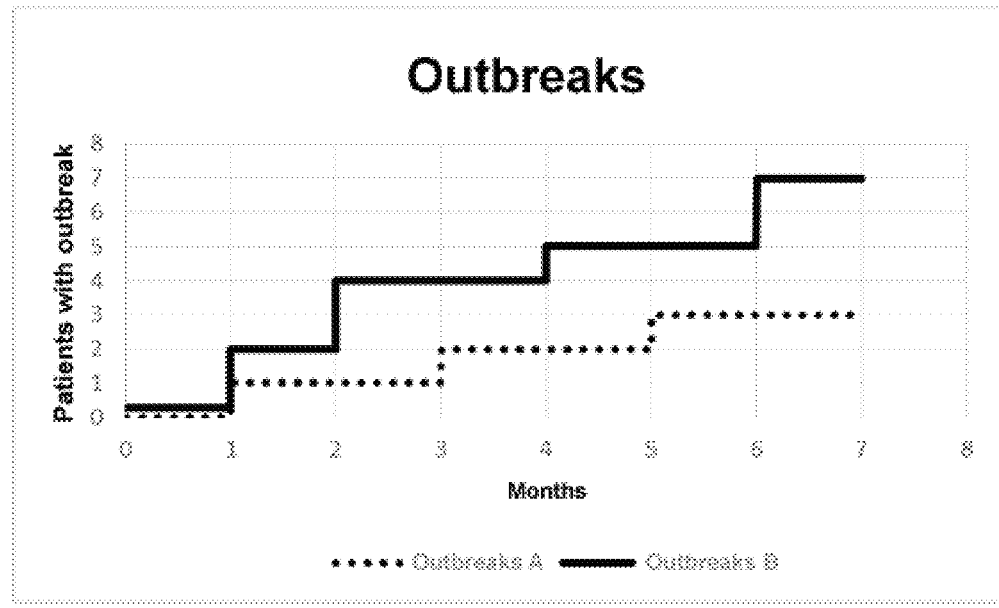
FIG. 10 is a graph showing the number of patients with a new psoriasis outbreak after median follow-up of six (6) months; group a, treated with the probiotic composition; group b treated with placebo.

After completion of treatment in the pilot study lasting twelve (12) weeks, a total of 38 patients of the total of 47 patients in the intervention study agreed to perform a follow up on a monthly basis for a total of six (6) months. During this follow up the PASI value of each patient was recorded and whether they had experienced a new outbreak of psoriasis. Patients who took the probiotic composition for three (3) months after stopping treatment had fewer new outbreaks after a mean follow-up of six (6) months, with significant differences when compared with the group of patients receiving placebo (3/19, 15.8% in the group taking the probiotic composition versus 7/19, 36.8% in the placebo group) (FIG. 10).

Figure 11:
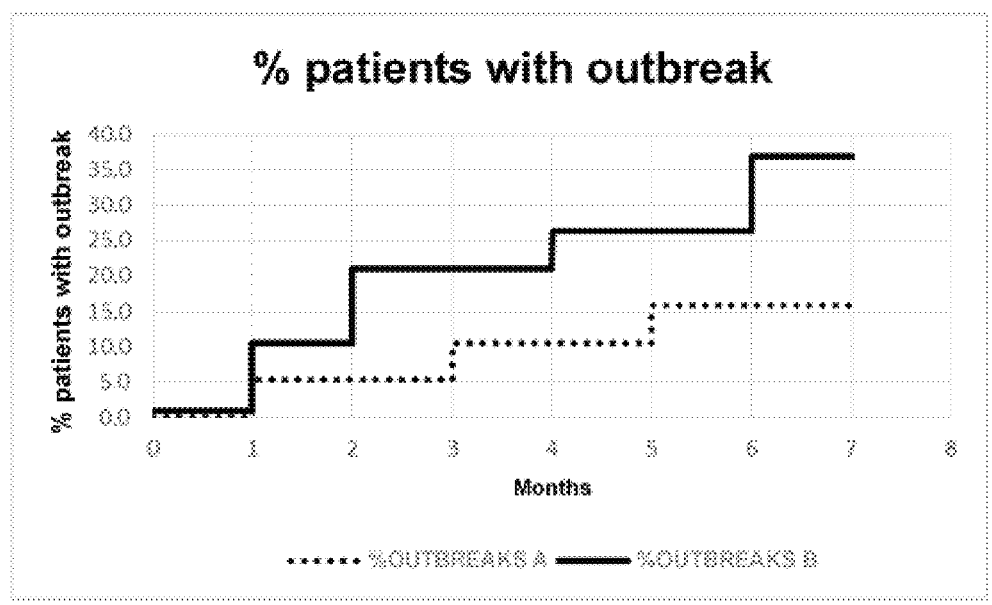
FIG. 11 is a graph showing the percentage of cases of relapse after receiving treatment for three (3) months with the probiotic composition vs. placebo: group a, treated with the probiotic composition; group b treated with placebo.

The percentage of cases with an early new outbreak (in the first two months of follow-up) was four (4) times higher in the placebo treatment group when compared with the group treated with the probiotic composition. There were four relapses (21%) in the placebo group against one relapse (5.2%) in the group treated with the probiotic composition at month 2 of follow-up and these differences between the two groups remained at the end of the period of six (6) months follow-up (FIG. 11).

2.3 Conclusion

It was concluded that a beneficial effect of the probiotic composition of the invention on the evolution of psoriasis was obtained, significantly increasing the percentage of patients with PASI 50, PASI 75 responses and fewer patients without response (PASI less than 50%) compared with patients who were not treated with the probiotic composition.

The invention claimed is:

1. A probiotic composition comprising microorganisms of *Bifidobacterium animalis* subs. *lactis* (*B. lactis*), *Bifidobacterium longum* and *Lactobacillus rhamnosus*, wherein the concentration of *B. longum* with respect to the total concentration of microorganisms present in the composition is at least 30%, wherein *B. lactis* is *B. lactis* CECT 8145, *B. longum* is *B. longum* ES1 CECT 7347 and *L. rhamnosus* is *L. rhamnosus* CECT 8361.

2. A method for the treatment or prevention of psoriasis outbreaks or psoriasis comprising administering to a subject in need thereof an effective amount of a probiotic composition comprising *Bifidobacterium animalis* subsp. *lactis* (*B. lactis*), *Bifidobacterium longum* and *Lactobacillus rhamnosus*, wherein *B. lactis* is *B. lactis* CECT 8145 is, *B. longum* is *B. longum* ES1 CECT 7347 and/or *L. rhamnosus* is *L. rhamnosus* CECT 8361.

3. The method according to claim 2, wherein the psoriasis outbreak or psoriasis is selected from the group consisting of plaque psoriasis, palmar-plantar psoriasis, scalp psoriasis, nail psoriasis, psoriasis on the face, psoriasis in the folds, guttate psoriasis, erythrodermic psoriasis and pustular psoriasis.

4. The method according to claim 2, wherein the probiotic composition is a pharmaceutical composition or a nutritional composition.

5. The method according to claim 4, wherein the pharmaceutical composition comprises a pharmaceutically acceptable carrier and/or an excipient.

6. The method according to claim 4, wherein the pharmaceutical composition is formulated for administration in liquid form or in solid form.

7. The method according to claim 6, wherein the solid formulation is selected from the group consisting of tablets, lozenges, sweets, chewable tablets, chewing gum, capsules, sachets, powders, granules, coated particles or coated tablets, tablets and gastro-resistant tablets and capsules and dispersible strips and films.

8. The method according to claim 6, wherein the liquid formulation is selected from the group consisting of oral solutions, suspensions, emulsions and syrups.

9. The method according to claim 4, wherein the nutritional composition is a food or a nutritional supplement.

10. The method according to claim 9, wherein the food is selected from the group consisting of fruit or vegetable juices, ice cream, infant formula, milk, yogurt, cheese, fermented milk, milk powder, cereals, baked goods, milk-based products, meat products and beverages.

11. The method according to claim 2, wherein the composition further comprises a microorganism selected from the group consisting of *Lactobacillus* sp., *Streptococcus* sp., *Bifidobacterium* sp., *Saccharomyces* sp., *Kluyveromyces* sp. and combinations thereof.

12. The method according to claim 2, wherein the total concentration of microorganisms of the strains *B. lactis*, *L. rhamnosus* and *B. longum* in the composition is between $10^3$ and $10^{12}$ cfu.

13. The method according to claim 2, wherein the concentration of *B. longum* with respect to the total concentration of microorganisms present in the composition is at least 30%.

* * * * *